United States Patent
Yamataka (10) Patent No.: US 10,849,544 B2
(45) Date of Patent: Dec. 1, 2020

(54) DRIVER CONDITION DETECTION DEVICE AND DRIVER CONDITION DETECTION METHOD

(71) Applicant: DENSO CORPORATION, Kariya (JP)

(72) Inventor: Minori Yamataka, Kariya (JP)

(73) Assignee: DENSO CORPORATION, Kariya (JP)

( * ) Notice: Subject to any disclaimer, the term of this patent is extended or adjusted under 35 U.S.C. 154(b) by 83 days.

(21) Appl. No.: 16/099,835

(22) PCT Filed: Apr. 12, 2017

(86) PCT No.: PCT/JP2017/014900
§ 371 (c)(1),
(2) Date: Nov. 8, 2018

(87) PCT Pub. No.: WO2017/203870
PCT Pub. Date: Nov. 30, 2017

(65) Prior Publication Data
US 2019/0110729 A1    Apr. 18, 2019

(30) Foreign Application Priority Data
May 23, 2016    (JP) ................. 2016-102221

(51) Int. Cl.
*G01C 22/00*    (2006.01)
*G05D 1/00*    (2006.01)
(Continued)

(52) U.S. Cl.
CPC .............. *A61B 5/18* (2013.01); *A61B 5/0077* (2013.01); *A61B 5/1116* (2013.01);
(Continued)

(58) Field of Classification Search
CPC ....... A61B 5/18; A61B 5/0077; A61B 5/1176; A61B 5/1495; A61B 5/4809; A61B 5/681;
(Continued)

(56) References Cited

U.S. PATENT DOCUMENTS 9,105,172 B2    8/2015    Kubotani et al.
2013/0021462 A1*    1/2013    Kadoya ............... A61B 5/18
                                                      348/78
(Continued)

FOREIGN PATENT DOCUMENTS

JP    2005-92285    4/2005
JP    2009-075648 A    4/2009
(Continued)

*Primary Examiner* — Mahmoud S Ismail
(74) *Attorney, Agent, or Firm* — Maschoff Brennan (57) ABSTRACT

A driver condition detection device for a vehicle includes: a physical information acquisition unit that acquires physical information of a driver; a standard setting unit that sets, as a standard range, the physical information in a case where the driver is in an operable state for driving the vehicle; a correspondence relationship accumulation unit that accumulates a correspondence relationship between a deviation of the physical information from the standard range and a time interval to return to the standard range; a recovery time estimation unit that estimates a recovery time to return to the standard range from the physical information acquired by the physical information acquisition unit, based on the correspondence relationship; and a determination unit that determines that the driver is in an inoperable state for driving the vehicle when the recovery time is more than a predetermined allowance time.

17 Claims, 6 Drawing Sheets

(51) Int. Cl.

| | | |
|---|---|---|
| *A61B 5/18* | (2006.01) | |
| *B60W 50/14* | (2020.01) | |
| *B60W 40/08* | (2012.01) | |
| *G08G 1/16* | (2006.01) | |
| *B60W 30/182* | (2020.01) | |
| *B60W 30/00* | (2006.01) | |
| *A61B 5/00* | (2006.01) | |
| *A61B 5/1495* | (2006.01) | |
| *A61B 5/11* | (2006.01) | |
| *A61B 5/1171* | (2016.01) | |
| *B60Q 9/00* | (2006.01) | |
| *B60W 50/08* | (2020.01) | |
| *A61B 5/0245* | (2006.01) | |
| *A61B 5/22* | (2006.01) | |
| *A61B 5/16* | (2006.01) | |

(52) U.S. Cl.
CPC .......... *A61B 5/1176* (2013.01); *A61B 5/1495* (2013.01); *A61B 5/4809* (2013.01); *A61B 5/681* (2013.01); *A61B 5/6891* (2013.01); *A61B 5/6893* (2013.01); *A61B 5/7264* (2013.01); *A61B 5/746* (2013.01); *B60Q 9/00* (2013.01); *B60W 30/00* (2013.01); *B60W 30/182* (2013.01); *B60W 40/08* (2013.01); *B60W 50/082* (2013.01); *B60W 50/14* (2013.01); *G05D 1/0061* (2013.01); *G08G 1/16* (2013.01); *A61B 5/0245* (2013.01); *A61B 5/163* (2017.08); *A61B 5/224* (2013.01); *A61B 5/7285* (2013.01); *A61B 2503/22* (2013.01); *A61B 2562/0247* (2013.01); *A61B 2562/0252* (2013.01); *B60W 2040/0872* (2013.01); *B60W 2050/143* (2013.01)

(58) Field of Classification Search
CPC ..... A61B 5/6891; A61B 5/7264; A61B 5/746; A61B 5/163; A61B 5/0245; A61B 5/224; A61B 5/7285; A61B 2503/22; A61B 2503/2562; A61B 2503/0252; B60Q 9/00; B60W 30/00; B60W 30/182; B60W 40/08; B60W 50/082; B60W 50/14; B60W 2040/0872; B60W 2050/143; G05D 1/0061; G08G 1/16
USPC .......................................................... 701/23
See application file for complete search history.

(56) References Cited

U.S. PATENT DOCUMENTS

| | | |
|---|---|---|
| 2016/0068103 A1 | 3/2016 | McNew et al. |
| 2016/0249180 A1* | 8/2016 | Li .................... G08G 1/096716 |
| 2016/0355190 A1 | 12/2016 | Omi |
| 2017/0140232 A1 | 5/2017 | Banno et al. |
| 2017/0364070 A1 | 12/2017 | Oba |
| 2019/0056732 A1* | 2/2019 | Aoi ...................... G05D 1/0061 |

FOREIGN PATENT DOCUMENTS

| | | |
|---|---|---|
| JP | 2011-164712 A | 8/2011 |
| JP | 2011-164825 A | 8/2011 |
| JP | 2012-245091 A | 12/2012 |
| JP | 2015-156877 A | 9/2015 |
| JP | 2016-009256 A | 1/2016 |
| JP | 2016-009257 A | 1/2016 |
| JP | 2016-071577 A | 5/2016 |
| JP | 2016-115356 A | 6/2016 |
| WO | 2011/118393 A1 | 9/2011 |

* cited by examiner

DRIVER CONDITION DETECTION DEVICE AND DRIVER CONDITION DETECTION METHOD

CROSS REFERENCE TO RELATED APPLICATION

This application is based on Japanese Patent Application No. 2016-102221 filed on May 23, 2016, the disclosure of which is incorporated herein by reference.

TECHNICAL FIELD

The present disclosure relates to a driver condition detection device and a driver condition detection method that detect a driving condition of a driver of a vehicle.

BACKGROUND ART

During driving of a vehicle, a driver may fall into a condition unable to continue driving (hereinbelow, referred to as an unable-to-drive condition) due to, for example, a sudden illness. A traffic accident caused by an unable-to-drive condition has conventionally been a problem. In order to prevent such a traffic accident, a technique that detects a driving condition of a driver (that is, whether the driver is in an unable-to-drive condition) has been developed.

For example, Patent Literature 1 proposes a technique that, in order to detect a driving condition of a driver, recognizes the direction of the face or the posture of the upper body of the driver from an image captured by a driver camera which is mounted on a vehicle and determines that the driver is in an unable-to-drive condition when the direction of the face or the posture of the upper body of the driver is deviated from a reference range.

PRIOR ART LITERATURES

Patent Literature

Patent Literature 1: JP-2016-9256-A

SUMMARY OF INVENTION

A driver may change the direction of the face or the posture of the upper body to check the surroundings of the vehicle. Further, there are differences between individuals in the direction of the face or the posture of the upper body of a driver in an unable-to-drive condition. Thus, there is a problem in that it is difficult to standardize a criterion for uniformly determining whether a driver is in an unable-to-drive condition from the direction of the face or the posture of the upper body of the driver, and it is necessary to individually set the criterion.

It is an object of the present disclosure to provide a driver condition detection device and a driver condition detection method that standardize a criterion for determining whether a driver is in an unable-to-drive condition.

According to a first aspect of the present disclosure, a driver condition detection device that detects a driving condition of a driver of a vehicle, the driver condition detection device includes: a physical information acquisition unit that acquires physical information of the driver, the physical information contributing to detection of the driving condition of the driver; a standard setting unit that sets, as a standard range, the physical information in a case where the driver is in an operable state for driving the vehicle; a correspondence relationship accumulation unit that accumulates a correspondence relationship between a deviation of the physical information from the standard range and a time interval to return to the standard range; a recovery time estimation unit that estimates a recovery time to return to the standard range from the physical information acquired by the physical information acquisition unit, based on the correspondence relationship; and a determination unit that determines that the driver is in an inoperable state for driving the vehicle when the recovery time is more than a predetermined allowance time.

In the above driver condition detection device, by using the recovery time estimated from the physical information of the driver, it is possible to uniformly determine whether the driver is in an unable-to-drive condition by comparison with the predetermined allowance time. Thus, it is not necessary to individually set the allowance time which is a criterion of determination, and it is possible to standardize the criterion.

According to a second aspect of the present disclosure, a driver condition detection method that detects a driving condition of a driver of a vehicle, the driver condition detection method includes: acquiring physical information of the driver, the physical information contributing to detection of the driving condition of the driver; setting, as a standard range, the physical information in a case where the driver is in an operable state for driving the vehicle; accumulating a correspondence relationship between a deviation of the physical information from the standard range and a time interval to return to the standard range; estimating a recovery time to return to the standard range from the physical information acquired in the acquiring of the physical information, based on the correspondence relationship; and determining that the driver is in an inoperable state for driving the vehicle when the recovery time is more than a predetermined allowance time.

In the above driver condition detection method, by using the recovery time estimated from the physical information of the driver, it is possible to uniformly determine whether the driver is in an unable-to-drive condition by comparison with the predetermined allowance time. Thus, it is not necessary to individually set the allowance time which is a criterion of determination, and it is possible to standardize the criterion.

BRIEF DESCRIPTION OF DRAWINGS

The above and other objects, features and advantages of the present disclosure will become more apparent from the following detailed description made with reference to the accompanying drawings. In the drawings.

EMBODIMENTS FOR CARRYING OUT INVENTION

Figure 1:
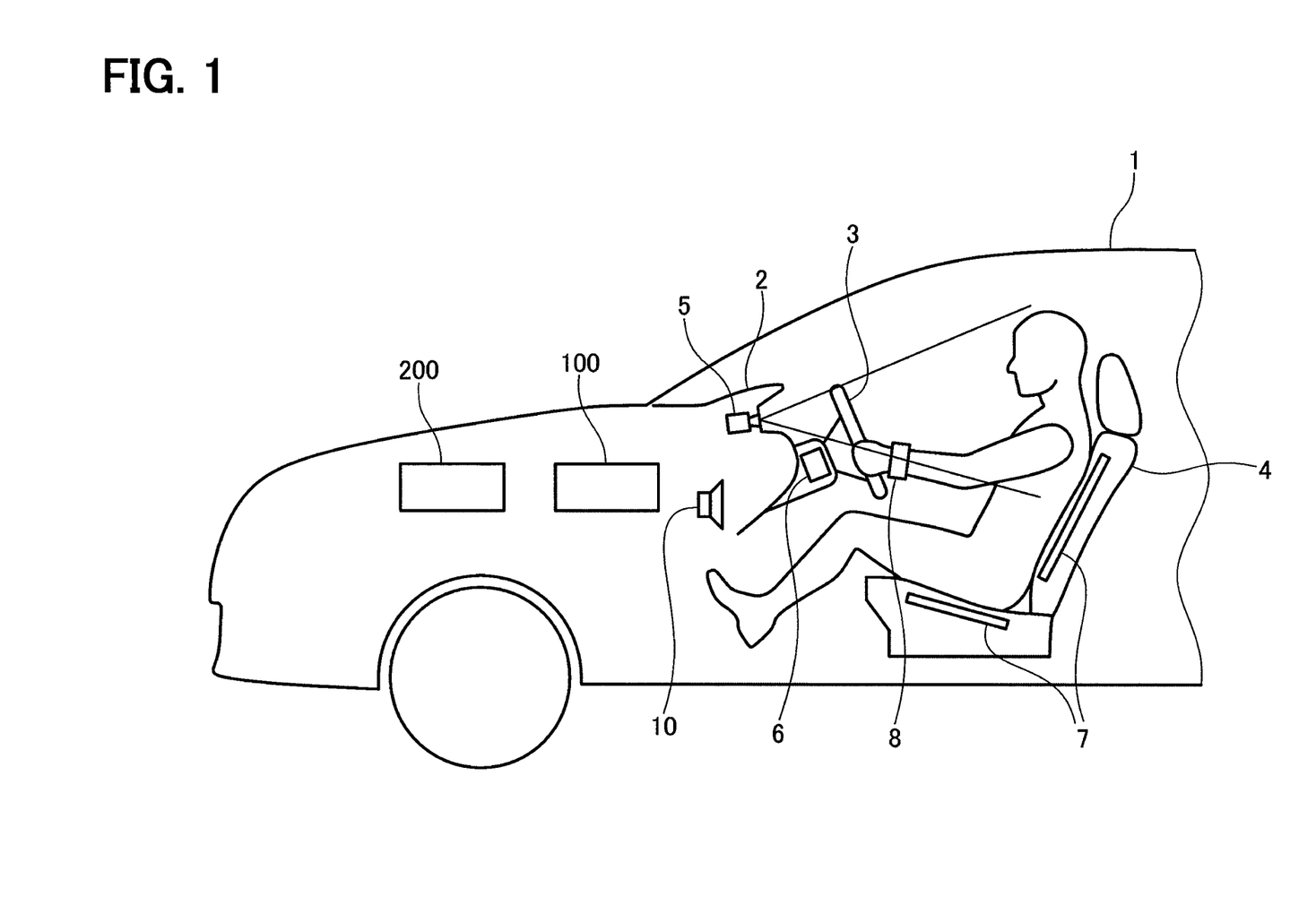
FIG. 1 is an explanatory diagram illustrating a general configuration of a vehicle equipped with a driver condition detection device of a present embodiment.

A. Device Configuration:

FIG. 1 illustrates a general configuration of a vehicle 1 which is equipped with a driver condition detection device 100 of a present embodiment. As illustrated, the vehicle 1 includes a driver camera 5, a steering wheel reaction force sensor 6, a seat pressure sensitive sensor 7, a pulsation sensor 8, a speaker 10, a vehicle control device 200, and the like in addition to the driver condition detection device 100.

The driver camera 5 is installed in a dashboard 2 of the vehicle 1 and capable of capturing an image of the upper body, including at least the face, of a driver.

The installation position of the driver camera 5 is not limited to the dashboard 2 as long as the driver camera 5 is capable of capturing an image of the driver. The driver camera 5 may be installed in a rearview mirror or a window pillar (so-called A pillar) which is located on each of right and left sides of a windshield. The driver camera 5 is not limited to one driver camera 5, and a plurality of driver cameras 5 may be installed.

The steering wheel reaction force sensor 6 detects a force that is applied to a shaft of a steering wheel 3 when the driver holds the steering wheel 3.

The seat pressure sensitive sensor 7 detects the distribution of a pressure that is applied to a seat surface and a backrest of a seat 4 on which the driver is seated.

The pulsation sensor 8 is a wristwatch type sensor which is worn around the wrist of the driver and detects the pulse (that is, the pulsation of the heart) of the driver. The pulsation sensor 8 is not limited to the sensor worn around the wrist as long as the pulsation sensor 8 is capable of detecting the pulsation of the heart of the driver. For example, a sensor may be installed in a part of a seatbelt, the part coming into contact with the chest of the driver, to detect the pulsation of the heart.

The speaker 10 is capable of emitting an alarm to the driver. A speaker connected to a music playback device which plays back music may be used as the speaker 10.

The vehicle control device 200 executes various control operations associated with driving of the vehicle 1. The vehicle 1 of the present embodiment is configured to be switchable between a manual driving mode in which the driver executes a driving operation such as an operation of the steering wheel 3, an operation of a brake, or an operation of an accelerator and an automatic driving mode in which the vehicle 1 autonomously executes the driving operation in place of the driver. The automatic driving mode is controlled by the vehicle control device 200.

The vehicle 1 may not necessarily have the automatic driving mode and may have a semi-autonomous type automatic driving mode in which the vehicle 1 executes part of the driving operation in place of the driver.

The driver condition detection device 100 detects a driving condition of the driver on the basis of physical information of the driver, such as a posture, a line of sight, and a consciousness level, acquired from the driver camera 5, the steering wheel reaction force sensor 6, the seat pressure sensitive sensor 7, and the pulsation sensor 8. When the driver condition detection device 100 determines that the driver is in a condition unable to drive the vehicle 1, the driver condition detection device 100 outputs the condition to the vehicle control device 200. Accordingly, the vehicle control device 200 takes safety measures such as stopping the vehicle 1.

Figure 2:
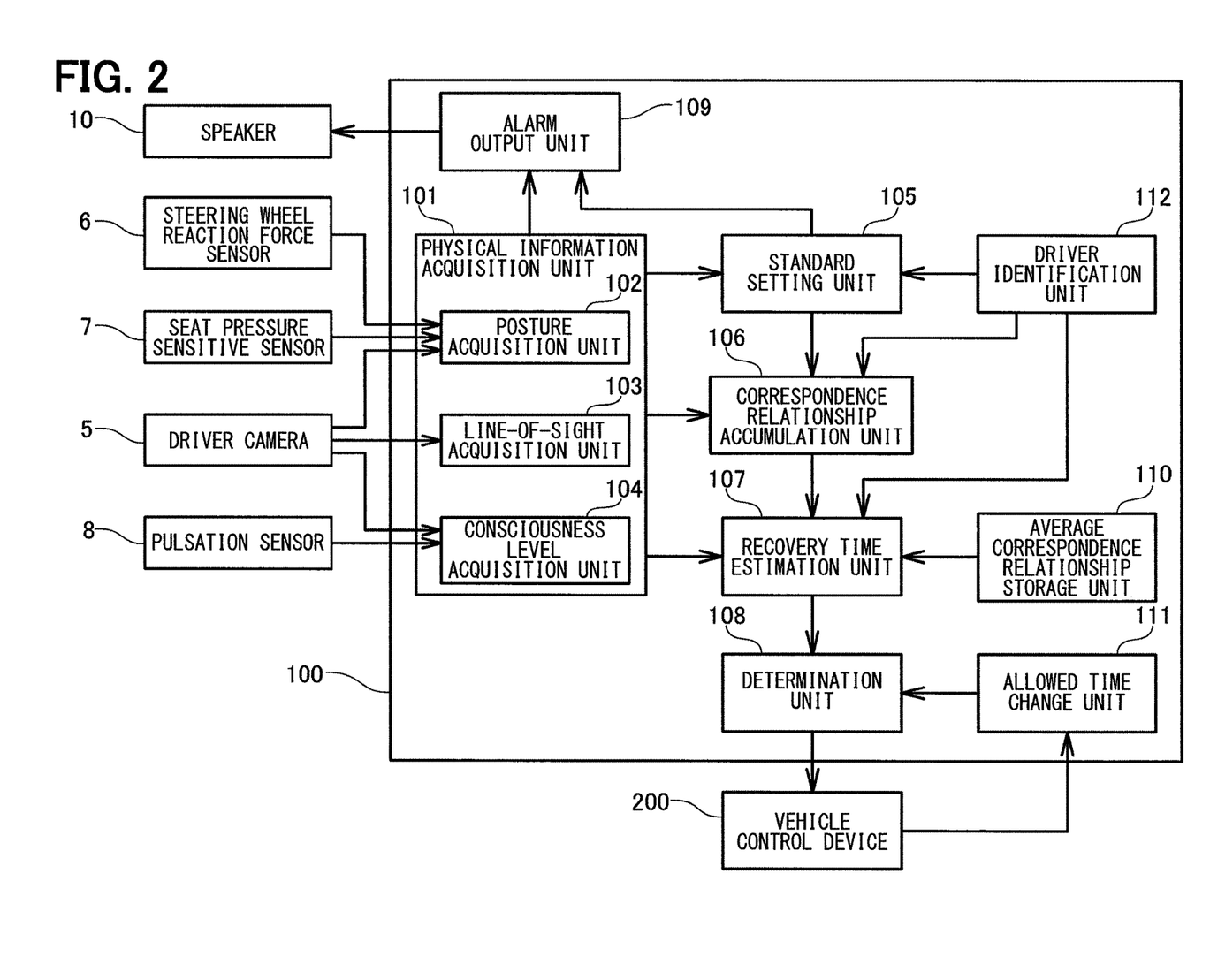
FIG. 2 is a block diagram illustrating the configuration of the driver condition detection device of the present embodiment.

FIG. 2 is a block diagram illustrating the configuration of the driver condition detection device 100 of the present embodiment. As illustrated, the driver condition detection device 100 includes a physical information acquisition unit 101, a standard setting unit 105, a correspondence relationship accumulation unit 106, a recovery time estimation unit 107, a determination unit 108, an alarm output unit 109, an average correspondence relationship storage unit 110, an allowed time change unit 111, and a driver identification unit 112.

The driver condition detection device 100 is conceptually classified into these "units" 101 to 112 by focusing on functions. These "units" 101 to 112 do not necessarily have to be physically independent of each other. These "units" 101 to 112 may include various devices, an electronic component, an integrated circuit, a computer, and a computer program, or a combination thereof.

The physical information acquisition unit 101 is connected to the driver camera 5, the steering wheel reaction force sensor 6, the seat pressure sensitive sensor 7, and the pulsation sensor 8, and acquires physical information of the driver.

The physical information acquisition unit 101 of the present embodiment includes a posture acquisition unit 102 which acquires a posture as physical information relating to an operation of the driver, a line-of-sight acquisition unit 103 which acquires a line of sight as physical information relating to recognition of the driver, and a consciousness level acquisition unit 104 which acquires a consciousness level as physical information relating to determination of the driver.

The posture acquisition unit 102 is connected to the driver camera 5, the steering wheel reaction force sensor 6, and the seat pressure sensitive sensor 7. The posture acquisition unit 102 acquires information about the posture of the upper body, including the face, of the driver from an image captured by the driver camera 5, acquires information about whether the driver is holding the steering wheel 3 on the basis of detection by the steering wheel reaction force sensor 6, and acquires information about a deviation of the center of gravity of the driver with respect to the seat 4 (e.g., a deviation to right or left of the seat surface or the degree of leaning against the backrest) on the basis of detection by the seat pressure sensitive sensor 7.

The line-of-sight acquisition unit 103 is connected to the driver camera 5. The line-of-sight acquisition unit 103 detects the eye of the driver from an image captured by the driver camera 5 to acquire information of the line of sight of the driver on the basis of the positional relationship between feature points of the eye. The feature points of the eye indicate organs of the eye and around the eye whose positions can be identified from the image, such as the iris (i.e., iris), the pupil, the outer canthus, the inner canthus, and the eyelid.

The consciousness level acquisition unit 104 is connected to the driver camera 5 and the pulsation sensor 8. The consciousness level acquisition unit 104 acquires the consciousness level of the driver, the consciousness level dropping due to a health problem or sleepiness, on the basis of an opening degree of the eyelid of the driver detected from an image captured by the driver camera 5 or the pulse of the driver detected by the pulsation sensor 8.

The standard setting unit 105 sets physical information in a case where the driver is able to drive the vehicle 1 as a standard range. In the present embodiment, driver information is registered when the driver drives the vehicle 1 for the first time. The standard setting unit 105 sets, as the standard range, physical information (that is, the posture, the line of sight, and the consciousness level) that is acquired by the physical information acquisition unit 101 under a condition of the driver suitable for driving the vehicle 1 at the registration of the driver information.

The standard range is not limited to a range having a predetermined limit width (e.g., an upper limit value and a lower limit value), and may be a specific value having matched upper and lower limit values, that is, a standard value.

The setting of the standard range of physical information is not limited to setting at the registration of the driver information. For example, an average of a plurality of pieces of physical information that are acquired by the physical information acquisition unit 101 while the driver is driving the vehicle 1 may be set as the standard range.

The correspondence relationship accumulation unit 106 accumulates the correspondence relationship between the difference between the physical information acquired by the physical information acquisition unit 101 and the standard range and the time to return to the standard range (that is, learns the correspondence relationship).

The recovery time estimation unit 107 estimates the time required to return to the standard range from the physical information acquired by the physical information acquisition unit 101 during traveling of the vehicle 1 (hereinbelow, referred to as a recovery time) on the basis of the correspondence relationship accumulated on the correspondence relationship accumulation unit 106.

When the recovery time estimated by the recovery time estimation unit 107 is within a predetermined allowed time (e.g., two seconds), the determination unit 108 determines that the driver is in a condition able to drive the vehicle 1. On the other hand, when the recovery time is more than the allowed time, the determination unit 108 determines that the driver is in a condition unable to drive the vehicle 1 and outputs the condition to the vehicle control device 200.

When the difference between the physical information acquired by the physical information acquisition unit 101 and the standard range is equal to or more than a predetermination value, the alarm output unit 109 transmits a data signal of an alarm to the speaker 10 to enable the speaker 10 to output the alarm.

The correspondence relationship accumulation unit 106 accumulates the correspondence relationship between the difference between the physical information that is acquired by the physical information acquisition unit 101 when the alarm is output and the standard range and the time required to return to the standard range.

The average correspondence relationship storage unit 110 previously stores an average correspondence relationship for each attribute of the driver (hereinbelow, referred to as the average correspondence relationship).

Examples of the attribute of the driver may include the age, the sex, the driving carrier, and the driving frequency of the driver. The average correspondence relationship is obtained by collecting the correspondence relationship between the difference between the physical information and the standard range and the time to return to the standard range from a large number of drivers and averaging the collected correspondence relationship for each attribute.

When the amount of correspondence relationship accumulated by the correspondence relationship accumulation unit 106 is less than a predetermined amount, the recovery time estimation unit 107 estimates the recovery time on the basis of the average correspondence relationship corresponding to the attribute of the driver.

The allowed time change unit 111 changes the allowed time which is a criterion of determination by the determination unit 108 according to whether the vehicle 1 is set to either the manual driving mode or the automatic driving mode. During the automatic driving mode, the driver is more relaxed than during the manual driving mode, and the difference between the physical information and the standard range thus tends to increase. Thus, the allowed time in the automatic driving mode is changed to a time (e.g., ten seconds) longer than the allowed time (e.g., two seconds) in the manual driving mode.

The allowed time change unit 111 is connected to the vehicle control device 200 and capable of grasping whether the vehicle 1 is in either the manual driving mode or the automatic driving mode.

The vehicle control device 200 of the present embodiment notifies the driver in advance of switching from the automatic driving mode to the manual driving mode. The correspondence relationship accumulation unit 106 accumulates the correspondence relationship between the difference between the physical information that is acquired by the physical information acquisition unit 101 when the switching is notified in advance and the standard range and the time required to return to the standard range.

The driver identification unit 112 identifies a plurality of drivers who may drive the vehicle 1 from one another. In the present embodiment, when a driver drives the vehicle 1 for the first time, the driver information is registered. The driver information includes a face image of the driver. The driver identification unit 112 compares a face image of a driver captured by the driver camera 5 with the registered driver information to identify the driver who drives the vehicle 1.

A method for identifying the driver is not limited to the comparison of the face image. For example, the driver who drives the vehicle 1 may select himself/herself from the plurality of registered drivers by an input operation by the driver himself/herself, and the driver identification unit 112 may identify the driver on the basis of the input operation.

The standard setting unit 105 sets the standard range of physical information for each of the drivers. The correspondence relationship accumulation unit 106 accumulates the correspondence relationship for each of the drivers.

The recovery time estimation unit 107 estimates the recovery time on the basis of the correspondence relationship for the driver who is driving the vehicle 1, the driver being identified by the driver identification unit 112.

Figure 3:
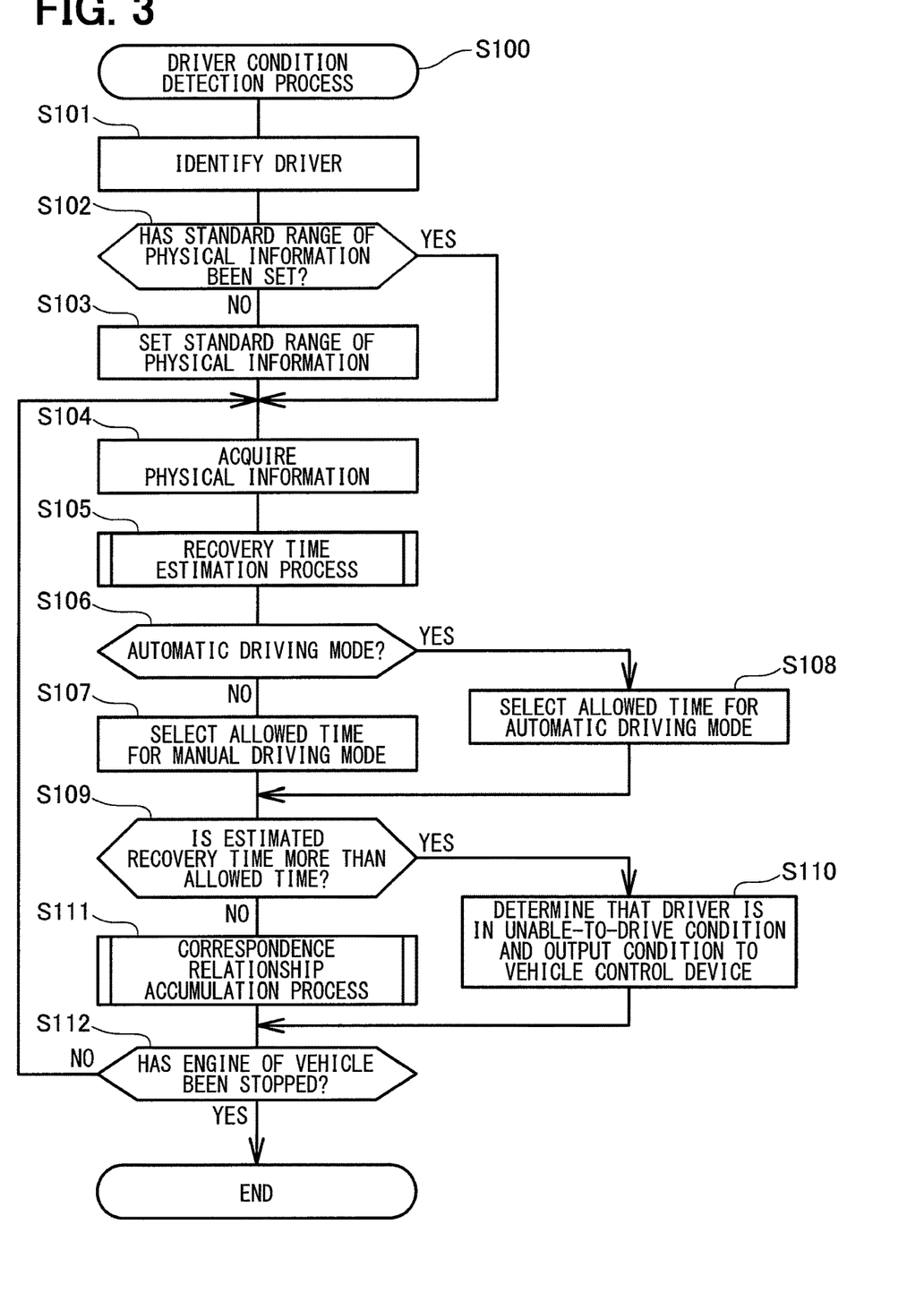
FIG. 3 is a flowchart illustrating a driver condition detection process which is executed by the driver condition detection device of the present embodiment.

B. Driver Condition Detection Process:

FIG. 3 is a flowchart of a driver condition detection process which is executed by the driver condition detection device 100 of the present embodiment.

The driver condition detection process (S100) is started when the driver activates the driver condition detection device 100. The driver condition detection process may be started in synchronization with an engine start of the vehicle 1. When the driver condition detection process (S100) is started, a face image of the driver captured by the driver camera 5 is first compared with the registered driver information to identity the driver who drives the vehicle 1 (S101).

Then, it is determined whether the standard range of physical information of the identified driver has been set (S102). As described above, in the present embodiment, physical information that is previously acquired under a condition of the driver suitable for driving the vehicle 1 is set as the standard range. When the standard range of physical information has not yet been set for the identified driver (S102: no), the standard range of physical information is set (S103).

On the other hand, when the standard range of physical information has already been set for the identified driver (S102: yes), the process of S103 is omitted, and physical information of the driver is acquired (S104).

As described above, in the present embodiment, the posture is acquired as physical information relating to an operation of the driver, the line of sight is acquired as physical information relating to recognition of the driver, and the consciousness level is acquired as physical information relating to determination of the driver.

After the physical information of the driver is acquired, a process of estimating a recovery time required to return to the standard range from the acquired physical information (hereinbelow, a recovery time estimation process) is started (S105).

Figure 4:
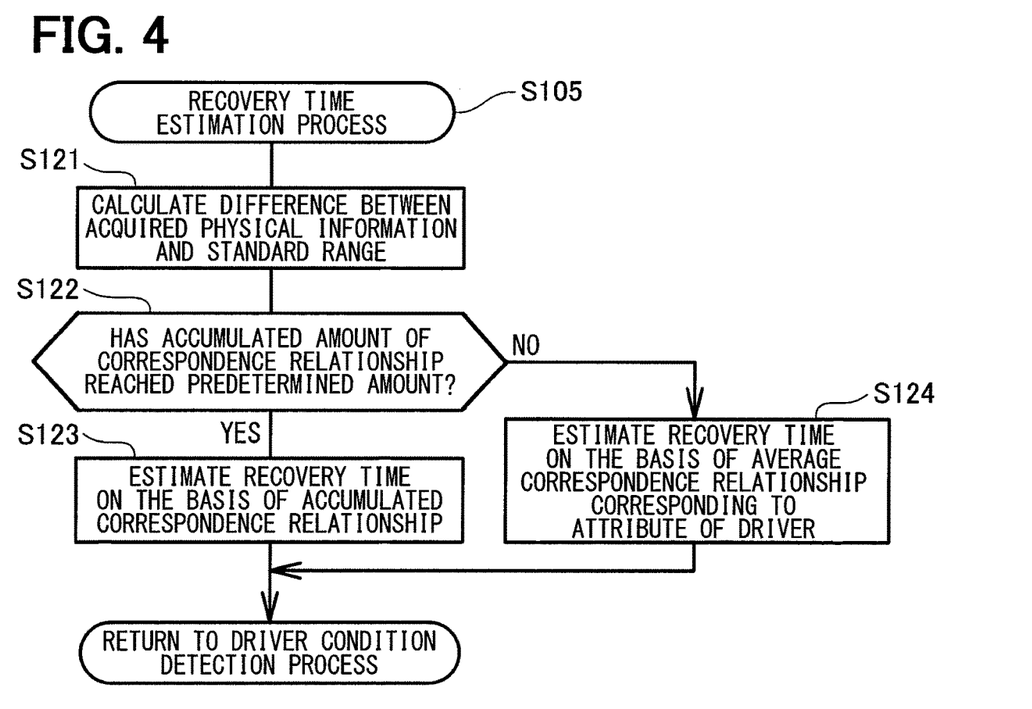
FIG. 4 is a flowchart illustrating a recovery time estimation process of the present embodiment.

FIG. 4 illustrates a flowchart of the recovery time estimation process. As illustrated, in the recovery time estimation process (S105), the difference between the acquired physical information and the standard range is first calculated (S121).

Figure 5:
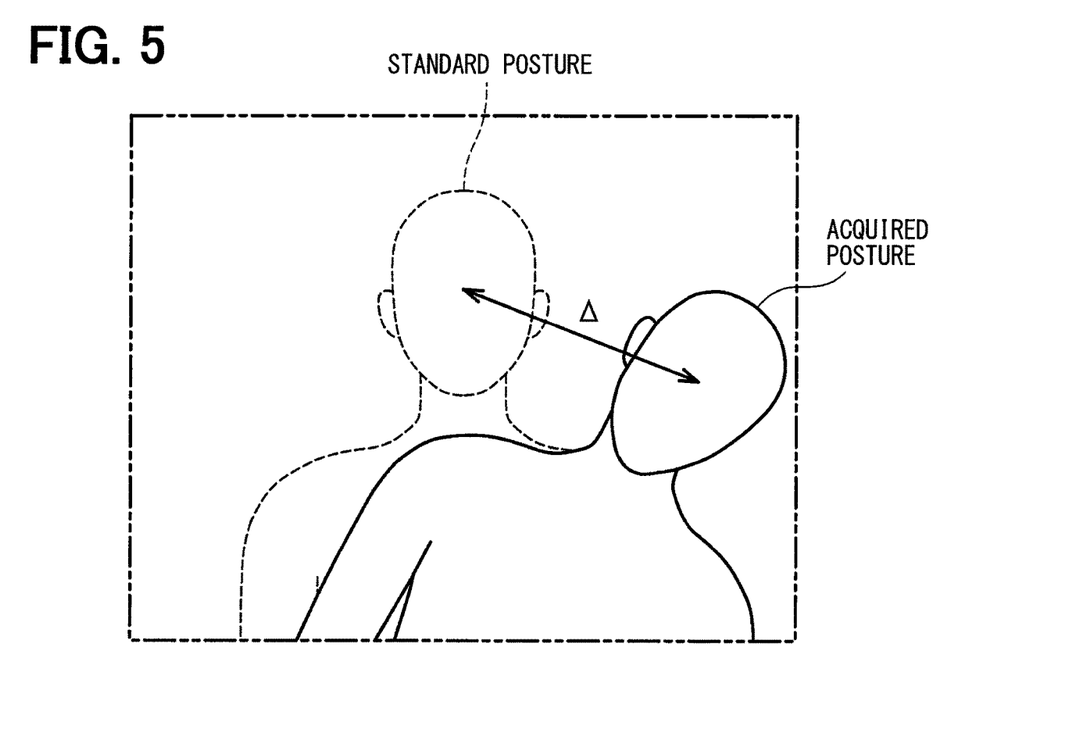
FIG. 5 is an explanatory diagram illustrating an example in which the posture of the upper body of a driver is deviated from a standard range.

For example, for the posture of the driver, as illustrated in FIG. 5, when the posture of the upper body, including the face, of the driver acquired from an image captured by the driver camera 5 (that is, an acquired posture indicated by a solid line in FIG. 5) is shifted from a posture of the upper body set as the standard range (that is, a standard posture indicated by a broken line in FIG. 5), a shift amount Δ thereof is calculated as the difference.

Figure 6A:
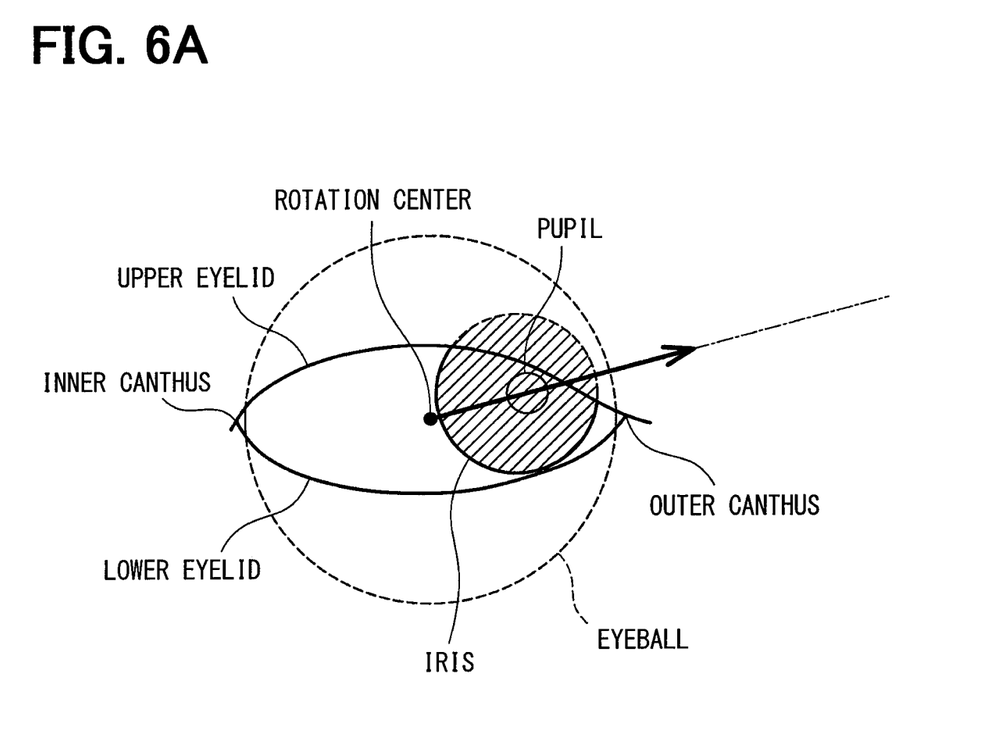
FIG. 6A and FIG. 6B are explanatory diagrams illustrating an example in which the line of sight of a driver is deviated from a standard range.
Figure 6B:
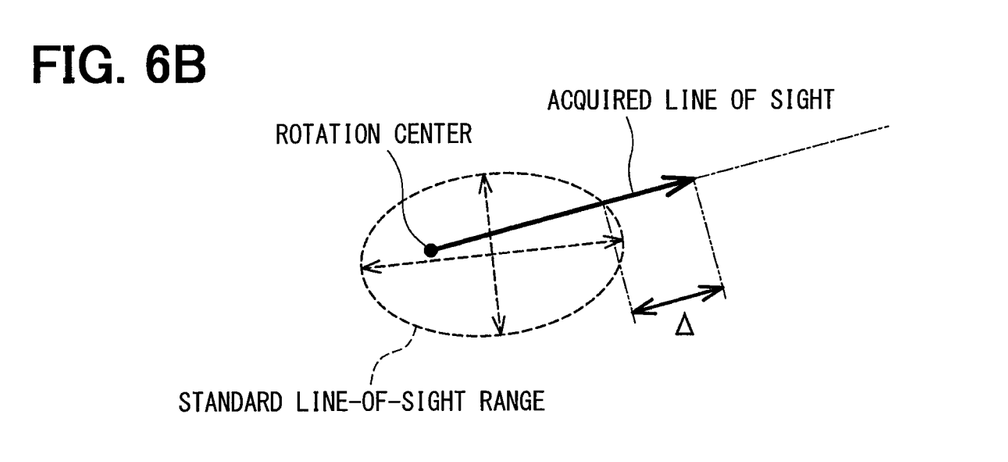

For the line of sight of the driver, as illustrated in FIG. 6A, a rotation center of the eyeball is estimated from the positional relationship between the feature points (that is, the iris, the pupil, the outer canthus, the inner canthus, and the upper and lower eyelids) of the face and the eye in an image captured by the driver camera 5, and a line that connects the rotation center with the pupil (or the center of the iris) is estimated as the line of sight. The driver who is driving the vehicle 1 checks safety while moving the line of sight. However, as illustrated in FIG. 6B, when the estimated line of sight of the driver (that is, an acquired line of sight indicated by a solid arrow in FIG. 6B) is shifted and deviated from a line-of-sight range which is set as the standard range (that is, a standard line-of-sight range indicated by a broken line in FIG. 6B), a shift amount Δ (e.g., a shift angle) thereof is calculated as the difference.

Further, the consciousness level of the driver may drop due to a health problem or sleepiness. The degree of the drop in the consciousness level manifests itself as the opening degree of the eyelid of the driver detected from an image captured by the driver camera 5 or the pulse of the driver detected by the pulsation sensor 8. Thus, when the acquired opening degree of the eyelid or pulse changes from the opening degree of the eyelid or pulse set as the standard range, a change amount thereof is calculated as the difference in the consciousness level.

Then, it is determined whether the accumulated amount of the correspondence relationship between the difference between the physical information and the standard range and the time to return to the standard range, the correspondence relationship being accumulated in a correspondence relationship accumulation process (S111) described below, has reached a predetermined amount (e.g., the number of accumulations is 100) (S122).

Then, when the accumulated amount of the correspondence relationship has reached the predetermined amount (S122: yes), the recovery time is estimated on the basis of the accumulated correspondence relationship (S123).

For example, as illustrated in FIG. 5, in the case where the acquired posture of the upper body of the driver is tilted with respect to the standard posture, when there is a similar situation in the accumulated correspondence relationship, the time required to return to the standard posture in the situation is referred to and added as the recovery time. When a speed of the movement of the upper body of the driver (that is, a movement amount of the upper body per unit time) is accumulated as the correspondence relationship, the time obtained by dividing the shift amount Δ from the acquired posture to the standard posture by the speed of the movement of the upper body may be added as the recovery time.

When the elbow of the driver is completely straightened, it is difficult to operate the steering wheel 3. Thus, when the degree of a bend of the arm of the driver can be detected from an image captured by the driver camera 5, the time to return to a posture with the elbow slightly bent which is set as the standard range, that is, the time required to return the posture is added to the recovery time.

Information about whether the driver is holding the steering wheel 3 is acquired on the basis of detection by the steering wheel reaction force sensor 6. When the driver is not holding the steering wheel 3, the time to hold the steering wheel 3 is added to the recovery time.

Information about a deviation of the center of gravity of the driver with respect to the seat 4 is acquired on the basis of detection by the seat pressure sensitive sensor 7. When the driver is seated leaning to either right or left of the seat surface or the driver leans against the backrest too much, the time to return to the position of the gravity center of the driver which is set as the standard range is added to the recovery time.

As illustrated in FIG. 6A and FIG. 6B, in the case where the acquired line of sight of the driver is shifted and deviated from the standard line-of-sight range, when there is a similar situation in the accumulated correspondence relationship, the time required to return to the standard line-of-sight range in the situation is referred to and added as the recovery time. When a speed of the movement of the line of sight of the driver (that is, the movement amount of the line of sight per unit time) is accumulated as the correspondence relationship, the time obtained by dividing the shift amount Δ from the acquired line of sight to the standard line-of-sight range by the speed of the movement of the line of sight may be added as the recovery time.

In the case where the consciousness level of the driver is acquired on the basis of the opening degree of the eyelid of the driver detected from an image captured by the driver camera 5 or the pulse of the driver detected by the pulsation sensor 8 and the consciousness level has dropped, when there is a similar situation in the accumulated correspondence relationship, the time required to return to the opening degree of the eyelid or pulse in the standard range in the situation is referred to and added as the recovery time.

Hereinabove, for avoiding complicated description, the description has been made assuming that the time required for each of the posture, the line of sight, and the consciousness level to recover is added. However, when the consciousness level drops, the operation of the driver tends to become slow, which affects the time to return to the standard range from the acquired posture or line of sight. Thus, a correction factor corresponding to the degree of a drop in the consciousness level may be multiplied so as to be added to the recovery time. As the consciousness level becomes lower, a larger value may be set as the correction factor.

In this manner, the recovery time may be estimated by a combination of a plurality of estimation grounds.

After the recovery time is estimated by comprehensively taking into consideration respective elements of the posture, the line of sight, and the consciousness level as the physical information of the driver on the basis of the accumulated correspondence relationship in this manner, the recovery time estimation process of FIG. 4 is finished, and the process returns to the driver condition detection process of FIG. 3.

On the other hand, when the accumulated amount of the correspondence relationship has not reached the predetermined amount in the determination of S122 of FIG. 4 (S122: no), the recovery time is estimated on the basis of the average correspondence relationship corresponding to the attribute of the driver.

As described above, in the present embodiment, the average correspondence relationship is previously stored for each of the age, the sex, the driving carrier, and the driving frequency as the attribute of the driver. The average correspondence relationship is obtained by collecting the correspondence relationship between the difference between the physical information and the standard range and the time to return to the standard range from a large number of drivers and averaging the collected correspondence relationship for each attribute. The average correspondence relationship may be multiplied by a predetermined safety factor.

The driver information that is registered when the driver drives the vehicle 1 for the first time includes the attribute of the driver such as the age, the sex, the driving carrier, or the driving frequency. The average correspondence relationship corresponding to the attribute of the driver identified in S101 of FIG. 3 is read out.

Also when the recovery time is estimated on the basis of the average correspondence relationship, in a manner similar to the case where the recovery time is estimated on the basis of the accumulated correspondence relationship described above (S123), the recovery time is estimated comprehensively taking into consideration respective elements of the posture (e.g., a tilt of the upper body, the degree of a bend of the arm, the presence or absence of holding of the steering wheel 3, or a deviation of the center of gravity), the line of sight, and the consciousness level (that is, the opening degree of the eyelid or the pulse) as the physical information of the driver.

For example, when a speed of a change of the physical information (that is, the posture, the line of sight, or the consciousness level) of the driver (that is, a change amount of the physical information per unit time) is stored as the average correspondence relationship, the time obtained by dividing the difference between the acquired physical information and the standard range by the speed of the change of the physical information may be added as the recovery time.

When the consciousness level drops, the time to return to the standard range from the acquired posture or line of sight tends to become long. Thus, a correction factor corresponding to the degree of the drop in the consciousness level may be multiplied so as to be added to the recovery time.

After the recovery time is estimated on the basis of the average correspondence relationship in this manner, the recovery time estimation process of FIG. 4 is finished, and the process returns to the driver condition detection process of FIG. 3.

In the driver condition detection process, after the process returns from the recovery time estimation process (S105), it is determined whether the vehicle 1 is in the automatic driving mode (S106). When the vehicle 1 is not in the automatic driving mode, that is, when the vehicle 1 is in the manual driving mode (S106: no), the allowed time for the manual driving mode (e.g., two seconds) is selected (S107).

On the other hand, when the vehicle 1 is in the automatic driving mode (S106: yes), the allowed time for the automatic driving mode (e.g., ten seconds) is selected (S108).

After the allowed time is selected according to whether the vehicle 1 is in either the automatic driving mode or the manual driving mode in this manner, it is then determined whether the recovery time estimated in S105 is more than the allowed time (S109). When the estimated recovery time is more than the allowed time (S109: yes), it is determined that the driver is in a condition unable to drive the vehicle 1, and the condition is output to the vehicle control device 200 (S110).

In response to the output, the vehicle control device 200 takes safety measures. For example, the vehicle control device 200 outputs a voice for checking the safety of the driver or forcibly stops the vehicle 1. When the vehicle 1 is in the automatic driving mode, the vehicle control device 200 outputs a voice for warning that there is unexpected switching to the manual driving mode or cancels switching from the automatic driving mode to the manual driving mode.

On the other hand, when the estimated recovery time is within the allowed time (S109: no), the correspondence relationship accumulation process is started (S111).

Figure 7:
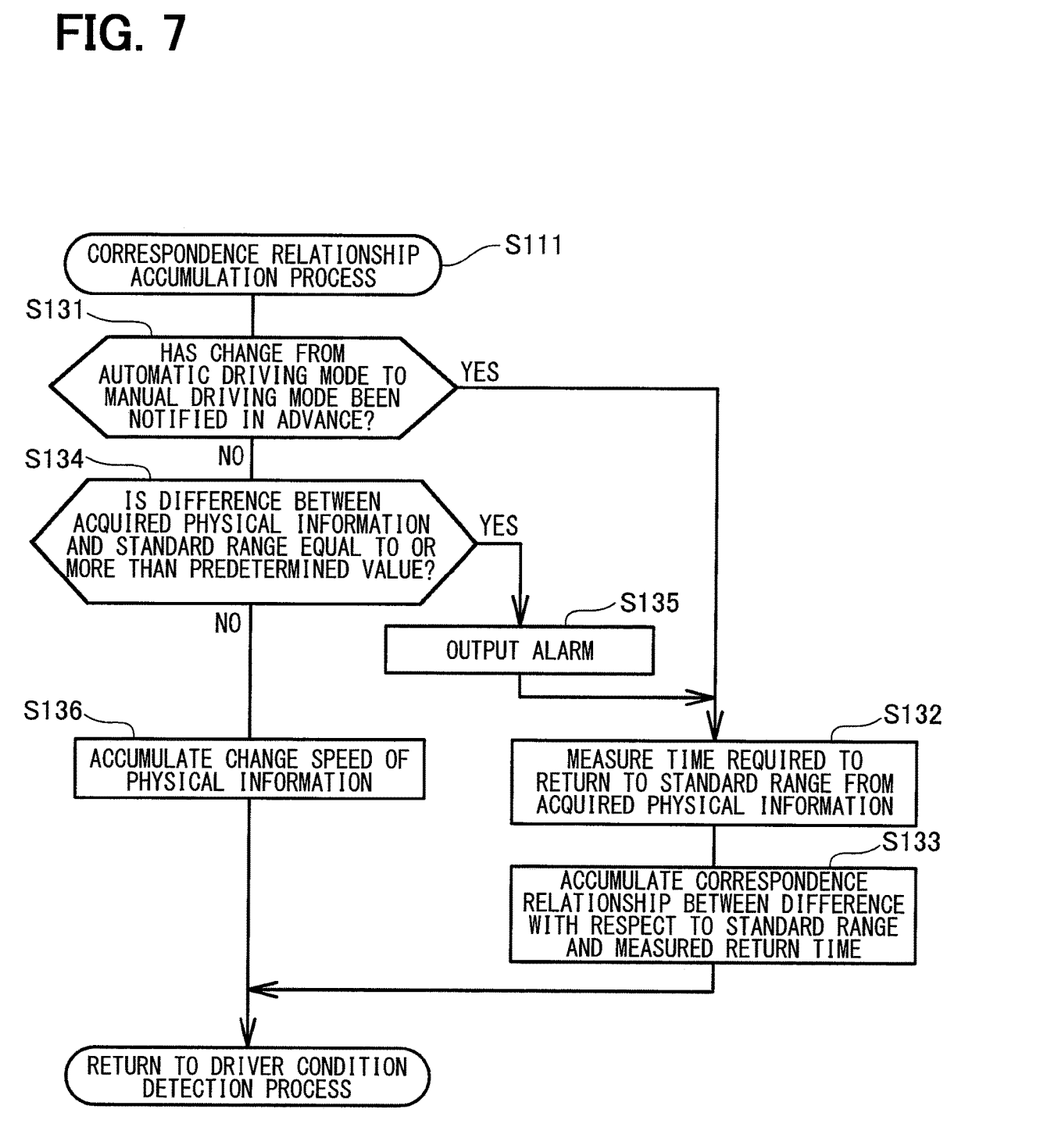
FIG. 7 is a flowchart illustrating a correspondence relationship accumulation process of the present embodiment.

FIG. 7 is a flowchart of the correspondence relationship accumulation process. As illustrated, in the correspondence relationship accumulation process (S111), it is first determined whether switching from the automatic driving mode to the manual driving mode has been notified in advance to the driver (S131). During the automatic driving mode, the driver is more relaxed than during the manual driving mode, and the physical information may thus be deviated from the standard range. When the switching from the automatic driving mode to the manual driving mode has been notified in advance (S131: yes), the driver tries to return to a condition suitable for driving the vehicle 1 (that is, the standard range of the physical information) from the relaxed state in preparation for a transfer of a driving authority from the vehicle 1 to the driver.

Thus, the time required to return to the standard range from the acquired physical information (hereinbelow, referred to as a return time) is measured (S132), and the correspondence relationship between the difference between the acquired physical information and the standard range and the return time is accumulated (S133). The correspondence relationship may be multiplied by a predetermined safety factor and accumulated.

For example, as illustrated in FIG. 5, when the acquired posture of the upper body of the driver is tilted with respect to the standard posture, a return time to the standard posture is measured, and the correspondence relationship is accumulated.

When the elbow of the driver is completely straightened, a return time to a posture with the elbow slightly bent which is set as the standard range is measured, and the correspondence relationship is accumulated.

When the driver is not holding the steering wheel 3, a return time to hold the steering wheel 3 is measured, and the correspondence relationship is accumulated.

When the driver is seated leaning to either right or left of the seat surface or the driver leans against the backrest too much, a recovery time to the position of the gravity center of the driver which is set as the standard range is measured, and the correspondence relationship is accumulated.

As illustrated in FIG. 6A and FIG. 6B, when the acquired line of sight of the driver is shifted and deviated from the standard line-of-sight range, a return time to the standard line-of-sight range is measured, and the correspondence relationship is accumulated.

When the consciousness level of the driver has dropped on the basis of the opening degree of the eyelid or the pulse of the driver, a return time to the opening degree of the eyelid or pulse in the standard range is measured, and the correspondence relationship is accumulated.

On the other hand, when the switching from the automatic driving mode to the manual driving mode has not been notified in advance in the determination of S131 (S131: no), it is determined whether the difference between the acquired physical information and the standard range is equal to or more than the predetermined value (S134). When the difference is equal to or more than the predetermined value (S134: yes), an alarm is output (S135). Accordingly, even when the physical information of the driver is unconsciously deviated from the standard range, with the alarm as a trigger, the driver who has noticed the deviation consciously tires to return to a condition suitable for driving the vehicle 1 (that is, the standard range of the physical information).

Thus, a return time required to return to the standard range from the acquired physical information is measured (S132), and the correspondence relationship between the difference between the acquired physical information and the standard range and the return time is accumulated (S133).

On the other hand, in a case where the difference between the acquired physical information and the standard range is less than the predetermined value (S134: no), when the physical information (that is, the posture, the line of sight, or the consciousness level) of the driver changes, a speed of the change of the physical information (that is, a change amount of the physical information per unit time) is accumulated as the correspondence relationship (S136).

After the correspondence relationship is accumulated in this manner, the correspondence relationship accumulation process of FIG. 7 is finished, and the process returns to the driver condition detection process of FIG. 3. Then, the accumulated correspondence relationship is used in estimation of the recovery time in the next and subsequent recovery time estimation process (S105 of FIG. 3) (S123 of FIG. 4).

In the driver condition detection process, after the process returns from the correspondence relationship accumulation process (S111), it is determined whether the engine of the vehicle 1 has been stopped (S112). When the engine of the vehicle 1 has not been stopped (S112: no), it is determined that the driver is continuously driving the vehicle 1, and the process returns to the process of S104 to acquire new physical information of the driver. Then, the series of following processes described above is executed again (S104 to S112).

When the engine of the vehicle 1 is stopped during the repetition of the process (S112: yes), it is determined that the driver has finished driving of the vehicle 1, and the driver condition detection process of FIG. 3 is finished.

As described above, in the driver condition detection device 100 of the present embodiment, physical information of a driver who is driving the vehicle 1 is acquired. The recovery time required to return to the standard range from the acquired physical information is estimated on the basis of the accumulated correspondence relationship. When the recovery time is more than the predetermined allowed time, it is determined that the driver is in a condition unable to drive the vehicle 1. By using the recovery time estimated from the physical information of the driver in this manner, it is possible to uniformly determine whether the driver is in an unable-to-drive condition by comparison with the predetermined allowed time. Thus, it is not necessary to individually set the allowed time which is a criterion of determination, and it is possible to standardize the criterion.

In the driver condition detection device 100 of the present embodiment, a reduction in an operation ability is reflected in the estimated recovery time by acquiring the posture as the physical information relating to an operation of the driver. Thus, it is possible to detect an unable-to-drive condition of the driver caused by the reduction in the operation ability.

A reduction in a recognition ability is reflected in the estimated recovery time by acquiring the line of sight as the physical information relating to recognition of the driver. Thus, it is possible to detect an unable-to-drive condition of the driver caused by the reduction in the recognition ability.

A reduction in a determination ability is reflected in the estimated recovery time by acquiring the consciousness level based on the opening degree of the eyelid or the pulse as the physical information relating to determination of the driver. Thus, it is possible to detect an unable-to-drive condition of the driver caused by the reduction in the determination ability.

It is possible to detect an unable-to-drive condition of the driver in various situations by compositely estimating the recovery time comprehensively taking into consideration the respective elements of the posture, the line of sight, and the consciousness level as the physical information of the driver.

In the driver condition detection device 100 of the present embodiment, it is possible to output an alarm to the driver when the acquired physical information is deviated from the standard range. With the alarm as a trigger, the time required for the driver to return the physical information to the standard range is measured, and the correspondence relationship is accumulated. Accordingly, it is possible to increase the accuracy of estimating the recovery time on the basis of the accumulated correspondence relationship.

In the driver condition detection device 100 of the present embodiment, the average correspondence relationship for each attribute of the driver is previously stored. When the accumulated amount of the correspondence relationship for the driver who is driving the vehicle 1 is less than the predetermined amount, the recovery time is estimated on the basis of the average correspondence relationship corresponding to the attribute of the driver who is driving the vehicle 1. Thus, it is possible to detect an unable-to-drive condition of the driver at an early stage when the correspondence relationship for the driver is not sufficiently accumulated.

The vehicle 1 of the present embodiment is configured to be switchable between the manual driving mode and the automatic driving mode. The allowed time in the automatic driving mode is changed to the time longer than the allowed time in the manual driving mode. During the automatic driving mode, it is assumed that the driver is more relaxed than during the manual driving mode, and the difference between the physical information and the standard range tends to increase. Thus, it is possible to appropriately detect an unable-to-drive condition of the driver also in the automatic driving mode by changing the allowed time to the allowed time for the automatic driving mode.

When switching from the automatic driving mode to the manual driving mode is notified in advance, the time required for the driver to return the physical information to the standard range is measured, and the correspondence relationship is accumulated. Accordingly, it is possible to increase the accuracy of estimating the recovery time on the basis of the accumulated correspondence relationship.

In the driver condition detection device 100 of the present embodiment, a plurality of drivers who may drive the vehicle 1 are identified from one another. The standard range of physical information is set for each of the drivers, and the correspondence relationship is accumulated for each of the drivers. Further, the recovery time is estimated on the basis of the correspondence relationship for the identified driver who is driving the vehicle 1. Thus, even when the vehicle 1 is shared between a plurality of drivers, it is possible to appropriately detect an unable-to-drive condition of each of the drivers.

For example, in the embodiment described above, the allowed time is changed between the manual driving mode and the automatic driving mode. However, the change of the allowed time is not limited thereto. For example, the allowed time may be changed according to the traveling speed of the vehicle 1. Specifically, as the traveling speed of the vehicle 1 increases, the time to ensure safety decreases. Thus, the allowed time may be reduced (that is, a strict criterion of determination may be used) to detect an unable-to-drive condition of the driver early.

It is noted that a flowchart or the processing of the flowchart in the present application includes sections (also referred to as steps), each of which is represented, for instance, as S101. Further, each section can be divided into several sub-sections while several sections can be combined into a single section. Furthermore, each of thus configured sections can be also referred to as a device, module, or means.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A driver condition detection device that detects a driving condition of a driver of a vehicle, the driver condition detection device comprising:
    a physical information acquisition unit that acquires physical information of the driver, the physical information contributing to detection of the driving condition of the driver;
    a standard setting unit that sets, as a standard range, the physical information in a case where the driver is in an operable state for driving the vehicle;
    a correspondence relationship accumulation unit that accumulates a correspondence relationship between a deviation of the physical information from the standard range and a time interval to return to the standard range;
    a recovery time estimation unit that estimates a recovery time to return to the standard range from the physical information acquired by the physical information acquisition unit, based on the correspondence relationship; and
    a determination unit that determines that the driver is in an inoperable state for driving the vehicle when the recovery time is more than a predetermined allowance time, wherein
    the vehicle is configured to be switchable between a manual driving mode in which the driver executes a driving operation and an automatic driving mode in which the vehicle executes at least a part of the driving operation in place of the drive;
    the driver condition detection device further comprising:
    an allowance time change unit that changes an allowance time in the automatic driving mode to be longer than an allowance time in the manual driving mode.

2. The driver condition detection device according to claim 1, wherein:
    the physical information acquisition unit includes a posture acquisition unit that acquires a posture of the driver as the physical information; and
    the recovery time estimation unit estimates the recovery time including a time to return to a standard posture set as the standard range from the posture of the driver acquired by the posture acquisition unit.

3. The driver condition detection device according to claim 1, wherein:
    the physical information acquisition unit includes a line-of-sight acquisition unit that acquires a line of sight of the driver as the physical information; and
    the recovery time estimation unit estimates the recovery time including a time to return to a standard line of sight set as the standard range from the line of sight of the driver acquired by the line-of-sight acquisition unit.

4. The driver condition detection device according to claim 1, wherein:
    the physical information acquisition unit includes a consciousness level acquisition unit that acquires a consciousness level of the driver as the physical information; and
    the recovery time estimation unit estimates the recovery time including a time to return to a standard consciousness level set as the standard range from the consciousness level of the driver acquired by the consciousness level acquisition unit.

5. The driver condition detection device according to claim 1, further comprising:
    an alarm output unit that outputs an alarm to the driver when the physical information acquired by the physical information acquisition unit is deviated from the standard range, wherein:
    the correspondence relationship accumulation unit accumulates the correspondence relationship between the deviation of the physical information, which is acquired by the physical information acquisition unit when the alarm is output, from the standard range and the time interval to return to the standard range.

6. The driver condition detection device according to claim 1, further comprising:
    an average correspondence relationship storage unit that preliminarily stores an average correspondence relationship that is an average of the correspondence relationship for each attribution of the driver, wherein:
    the recovery time estimation unit estimates the recovery time based on the average correspondence relationship corresponding to the attribution of the driver when an accumulated amount of the correspondence relationship accumulated by the correspondence relationship accumulation unit is less than a predetermined value.

7. The driver condition detection device according to claim 1, wherein:
    the vehicle is configured to be switchable between a manual driving mode in which the driver executes a driving operation and an automatic driving mode in which the vehicle executes at least a part of the driving operation in place of the driver; and the correspondence relationship accumulation unit accumulates the correspondence relationship between the deviation of the physical information, which is acquired by the physical information acquisition unit when switching from the automatic driving mode to the manual driving mode is notified in advance, from the standard range and a time interval to return to the standard range.

8. The driver condition detection device according to claim 1, further comprising:
a driver identification unit that identifies the driver among a plurality of drivers who drive the vehicle, wherein:
the standard setting unit sets the standard range for each of the drivers;
the correspondence relationship accumulation unit accumulates the correspondence relationship for each of the drivers; and
the recovery time estimation unit estimates the recovery time based on the correspondence relationship of the driver who is driving the vehicle and identified by the driver identification unit.

9. A driver condition detection method that detects a driving condition of a driver of a vehicle, the driver condition detection method comprising:
acquiring physical information of the driver, the physical information contributing to detection of the driving condition of the driver;
setting, as a standard range, the physical information in a case where the driver is in an operable state for driving the vehicle;
accumulating a correspondence relationship between a deviation of the physical information from the standard range and a time interval to return to the standard range;
estimating a recovery time to return to the standard range from the physical information acquired in the acquiring of the physical information, based on the correspondence relationship; and
determining that the driver is in an inoperable state for driving the vehicle when the recovery time is more than a predetermined allowance time, wherein
the vehicle is configured to be switchable between a manual driving mode in which the driver executes a driving operation and an automatic driving mode in which the vehicle executes at least a part of the driving operation in place of the driver; and
the driver condition detection device further comprising:
changing an allowance time in the automatic driving mode to be longer than an allowance time in the manual driving mode.

10. A driver condition detection device for detecting a driving condition of a driver of a vehicle, the vehicle switchable between a manual driving mode in which the driver executes a driving operation and an automatic driving mode in which the vehicle executes at least a part of the driving operation in place of the driver, the driver condition detection device comprising:
a computer that is configured to:
acquire physical information of the driver, the physical information contributing to detection of the driving condition of the driver;
set, as a standard range, the physical information in a case where the driver is in an operable state for driving the vehicle;
accumulate a correspondence relationship between a deviation of the physical information from the standard range and a time interval to return to the standard range;
estimate a recovery time to return to the standard range from the physical information that is acquired, based on the correspondence relationship;
determine that the driver is in an inoperable state for driving the vehicle when the recovery time is more than a predetermined allowance time; and
change an allowance time in the automatic driving mode to be longer than an allowance time in the manual driving mode.

11. The driver condition detection device according to claim 10, the computer further configured to:
acquire a posture of the driver as the physical information; and
estimate the recovery time including a time to return to a standard posture set as the standard range from the posture of the driver that is acquired.

12. The driver condition detection device according to claim 10, the computer further configured to:
acquire a line of sight of the driver as the physical information; and
estimate the recovery time including a time to return to a standard line of sight set as the standard range from the line of sight of the driver that is acquired.

13. The driver condition detection device according to claim 10, the computer further configured to:
acquire a consciousness level of the driver as the physical information; and
estimate the recovery time including a time to return to a standard consciousness level set as the standard range from the consciousness level of the driver that is acquired.

14. The driver condition detection device according to claim 10, the computer further configured to:
output an alarm to the driver when the physical information is deviated from the standard range; and
accumulate the correspondence relationship between the deviation of the physical information, which is acquired when the alarm is output, from the standard range and the time interval to return to the standard range.

15. The driver condition detection device according to claim 10, further comprising:
an average correspondence relationship storage unit that preliminarily stores an average correspondence relationship that is an average of the correspondence relationship for each attribution of the driver,
the computer further configured to:
estimate the recovery time based on the average correspondence relationship corresponding to the attribution of the driver when an accumulated amount of the correspondence relationship is less than a predetermined value.

16. The driver condition detection device according to claim 10, wherein:
the vehicle is configured to be switchable between a manual driving mode in which the driver executes a driving operation and an automatic driving mode in which the vehicle executes at least a part of the driving operation in place of the driver; and
the computer further configured to:
accumulate the correspondence relationship between the deviation of the physical information, which is acquired when switching from the automatic driving mode to the manual driving mode is notified in advance, from the standard range and a time interval to return to the standard range.

17. The driver condition detection device according to claim 10, the computer further configured to:
- identify the driver among a plurality of drivers who drive the vehicle;
- set the standard range for each of the drivers;
- accumulate the correspondence relationship for each of the drivers; and
- estimate the recovery time based on the correspondence relationship of the driver who is driving the vehicle and identified.

* * * * *